US009084535B2

(12) United States Patent
Girkin et al.

(10) Patent No.: US 9,084,535 B2
(45) Date of Patent: Jul. 21, 2015

(54) NON-IONIZING IMAGER

(75) Inventors: John Michael Girkin, Glasgow (GB); Simon Poland, Glasgow (GB); Christopher Longbottom, Dundee (GB)

(73) Assignee: King's College London, London (GB)

( * ) Notice: Subject to any disclaimer, the term of this patent is extended or adjusted under 35 U.S.C. 154(b) by 720 days.

(21) Appl. No.: 12/594,095

(22) PCT Filed: Mar. 28, 2008

(86) PCT No.: PCT/GB2008/001085
§ 371 (c)(1),
(2), (4) Date: Sep. 30, 2009

(87) PCT Pub. No.: WO2008/119964
PCT Pub. Date: Oct. 9, 2008

(65) Prior Publication Data
US 2010/0137722 A1    Jun. 3, 2010

(30) Foreign Application Priority Data

Mar. 30, 2007   (GB) .................................. 0706155.9

(51) Int. Cl.
*A61B 6/14*       (2006.01)
*A61B 5/00*       (2006.01)
*G01N 21/49*      (2006.01)
*G01N 21/359*     (2014.01)
*G01N 21/47*      (2006.01)

(52) U.S. Cl.
CPC .............. *A61B 5/0088* (2013.01); *A61B 5/0082* (2013.01); *G01N 21/49* (2013.01); *G01N 21/359* (2013.01); *G01N 2021/4707* (2013.01); *G01N 2021/4719* (2013.01); *G01N 2201/1053* (2013.01); *G01N 2201/1085* (2013.01)

(58) Field of Classification Search
USPC ............ 250/336.1, 358.1; 356/335, 497, 511, 356/72, 551; 600/160, 315, 473
See application file for complete search history.

(56) References Cited

U.S. PATENT DOCUMENTS

| 4,651,002 A | * | 3/1987 | Anno ......................... 250/336.1 |
| 4,945,239 A | * | 7/1990 | Wist et al. .................. 250/358.1 |
| 5,570,182 A | * | 10/1996 | Nathel et al. .................. 356/511 |

(Continued)

FOREIGN PATENT DOCUMENTS

| JP | 2006133499 A | 5/2006 |
| WO | WO 00/16691 A1 | 3/2000 |

(Continued)

OTHER PUBLICATIONS

Jones et al, Transillumination of Interproximal Caries Lesions with 830-nm Light, SPIE vol. 5313, Bellingham, WA, 2004.*

(Continued)

*Primary Examiner* — Unsu Jung
*Assistant Examiner* — Serkan Akar
(74) *Attorney, Agent, or Firm* — Alston & Bird LLP

(57) ABSTRACT

A medical imager, primarily for use in oral and dental applications. The imager has a source for providing a plurality of collimated beams of non-ionizing radiation, in particular near-infrared light, and a plurality of correlated detectors. Each detector is arranged to receive unscattered light from one or part of one of said collimated beams and scattered light from one or more other beams. The imager further comprises means for using both the unscattered and scattered light to form an image.

20 Claims, 1 Drawing Sheet

(56) References Cited

U.S. PATENT DOCUMENTS

| | | | |
|---|---|---|---|
| 6,193,401 B1* | 2/2001 | Girkin et al. | 362/551 |
| 6,243,601 B1* | 6/2001 | Wist | 600/473 |
| 6,485,413 B1* | 11/2002 | Boppart et al. | 600/160 |
| 7,365,859 B2* | 4/2008 | Yun et al. | 356/497 |
| 7,796,243 B2* | 9/2010 | Choo-Smith et al. | 356/72 |
| 2004/0246479 A1* | 12/2004 | Cartlidge et al. | 356/335 |
| 2005/0283058 A1* | 12/2005 | Choo-Smith et al. | 600/315 |
| 2008/0062429 A1* | 3/2008 | Liang et al. | 356/497 |
| 2010/0137722 A1* | 6/2010 | Girkin et al. | 600/473 |

FOREIGN PATENT DOCUMENTS

| | | |
|---|---|---|
| WO | WO 03/021329 A2 | 3/2003 |
| WO | WO 03/069391 A1 | 8/2003 |
| WO | WO 2005/013843 A2 | 2/2005 |

OTHER PUBLICATIONS

Fainman et al, 3-D Quantitative Imaging of the Microvasculature with the Texas Instruments Digital Micromirror Device, Proceedings of SPIE vol. 4457, 2001.*

Taylor et al, Effects of source coherence and aperture array geometry on optical sectioning strength in direct-view microscopy, J. Opt. Soc. Am. A/vol. 19, No. 7, Jul. 2002.*

Jones, G. C. et al., *Transillumination of Interproximal Caries Lesions With 830-nm Light*, Lasers in Denistry X, Proceedings of SPIE vol. 5313, No. 1, Jan. 1, 2004, pp. 17-22.

Wist, A. O. et al., *A New Transillumination System for the Correct Assessment of Covered Caries Lesions and Root Canals in Teeth*, Proceedings of the 22$^{nd}$ Annual EMBS International Conference, Jul. 23-28, 2000, Chicago, IL; IEEE, 2000, pp. 1036-1039.

Buhler, C. M. et al., *Imaging of Occlusal Dental Caries (Delay) With Near-IR Light at 1310-nm*, Optics Express, vol. 13, Issue 2, 2005, pp. 573-582.

Jiang, H. et al., *Three-Dimensional Optical Tomographic Imaging of Breast in a Human Subject*, IEEE Transactions on Medical Imaging, vol. 20, No. 12, (Dec. 2001). 1334-1340.

Zhang, Q. et al., *Three-Dimensional Diffuse Optical Imaging of Hand Joints: System Description and Phantom Studies*, Optics and Lasers in Engineering 43 (2005) 1237-1251.

Examination Report for Application No. EP 08 718 915.5 dated Sep. 7, 2012.

* cited by examiner

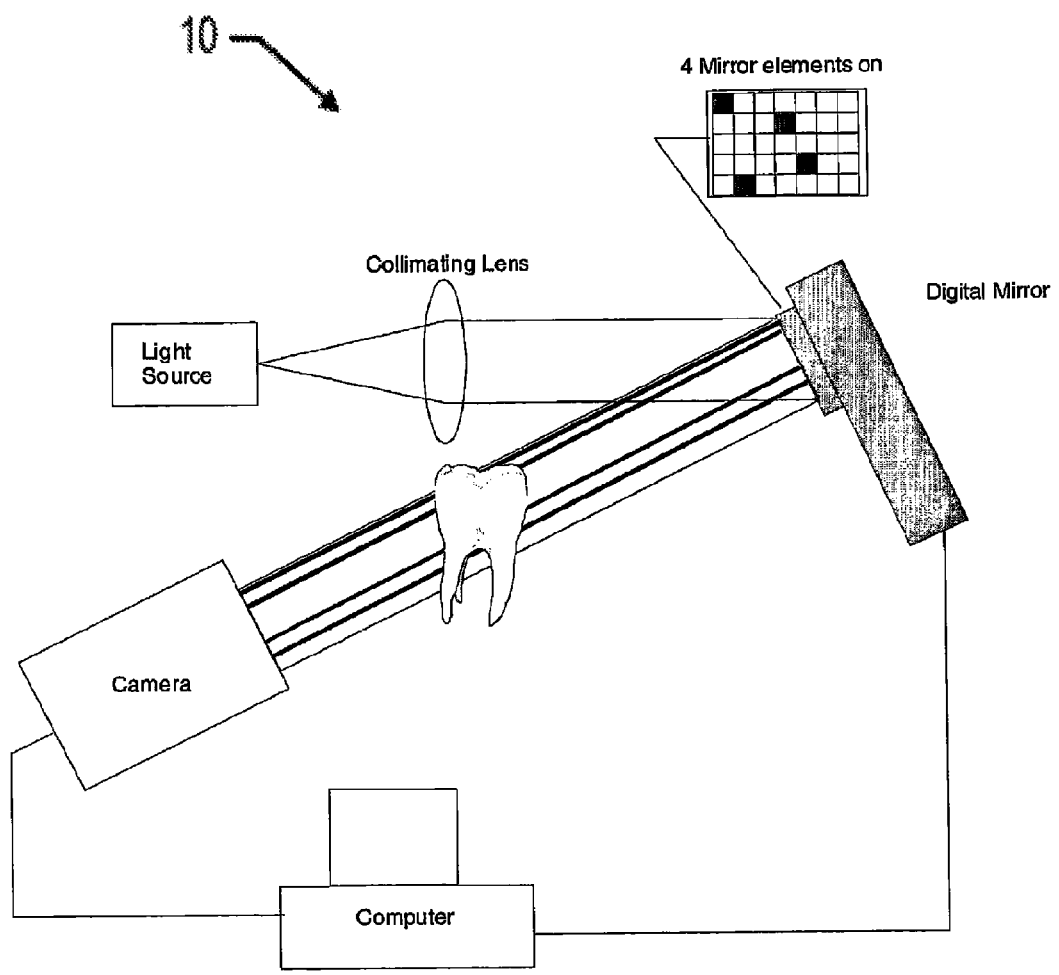

NON-IONIZING IMAGER

The present invention relates to a non-ionizing imager, primarily for use in oral and dental, medical and veterinary applications. In particular, the present invention relates to an infrared or near infrared imager.

X-rays are widely used for dental assessment of the developing occlusion and tooth structure. However, X-ray imaging carries with it well known health hazards and the dosage has to be kept within defined limits. This means that it is generally not possible for clinicians to take multiple images. The health hazards are a particular problem for young patients, who may be more sensitive to the negative effects of X-ray exposure.

To avoid some of the problems with X-ray imaging, Wist et al developed an imager for imaging individual teeth using a point-scanned system, see for example "A new Transillumination System for the Correct Assessment of Covered Caries Lesions and Root Canals in Teeth" A O Wist, R Sterne, P Moon, Proc Spie 2329 1994. Daniel Fried and John Featherstone have also undertaken imaging using IR light of dental tissue, see Optics Express 13 573 2005. However, neither of these systems is practical for in vivo applications due mainly to the time required to build an image and the related potential for tissue movement. In addition, the placing of scanning components in the oral cavity or elsewhere is a non-trivial challenge.

According to the present invention, there is provided a non-scanning medical imager that has a source for providing a plurality of collimated beams of non-ionizing radiation and a plurality of correlated detectors, each detector being arranged to receive unscattered light from one or part of one of said collimated beams and scattered light from one or more other beams. The imager is preferably operable to distinguish between the unscattered and scattered light. The imager may further comprise means for using both the unscattered and scattered light to form an image.

By using a plurality of collimated beams of non-ionizing radiation, and detecting both unscattered and scattered radiation, the present invention offers the ability to take multiple high-resolution images giving the same or better information, without the hazard of multiple exposures to X-ray. For oral and dental applications this opens up the possibility of routine imaging of every tooth at every dental check-up, which could improve early detection of caries and facilitate optimal preventive and operative therapy. It also allows for the imaging of the jaws for the developing dentition, which would be of enormous clinical benefit in children's and orthodontic assessments, as well as monitoring tissue during endo-dontic and periodontal therapy.

The source may be laser, LED or thermal source and may be pixelated or be directed onto a device that produces an array of "beamlets". Each beamlet is correlated with a pixelated or point scanned detector, so that it would be expected to land on one or more corresponding pixels if there was no deviation of the beamlet between the source and detector.

All of the individual beamlets or patterns may be switched on simultaneously for complete coverage of the sample. Alternatively, one or more selected groups of pixels may be switched on.

Preferably, the non-ionizing radiation is infrared radiation. Light around 810 nm may be used. This has advantages for oral and dental applications in that it can be well transmitted through teeth but undergoes sufficient scattering if a change in the optical properties of the tooth, for example, is present. Radiation having a wavelength of 810 nm is also well detected by Si based detectors offering the possibility of low cost and light efficient systems.

Light may be used to undertake differential spectroscopic imaging to distinguish oxygenated and de-oxygenated blood. The light for doing this may be in the range of around 810 nm and 850 nm. The use of wavelengths for identifying and quantifying the presence of blood and/or small blood vessels in particular regions of an image may be of value in identifying regions of inflammation, thereby indicating potential areas of pathological change.

There may, however, be advantages in moving to longer wavelengths for some tissue types. For example, for high contrast images of teeth, a preferred wavelength range is 1100 nm to 1300 nm. Wavelengths for imaging bone, muscle, skin and other soft tissues are in the NIR, to allow imaging of the jaws.

The light may be temporally coherent or not, although spatial coherence may need to be removed to prevent problems on the detector.

One or more filters may be used with the source to preferentially select the incident light. The one or more filters may be used with the detector to remove background light.

For convenience the light source and or detector may be located some distance from the object to be imaged where suitable means can be used to transmit the beamlets to and/or from the points on either side of the object. This means that the system could be used endoscopically with arrayed fibres delivering and/or receiving the light from a remote source/detector. These fibres need not be a coherent bundle as fibre emission can be "mapped" onto the detector.

According to another aspect of the invention, there is provided a method of diagnosis of the human or animal body that uses images derived using the system or method of any of the preceding claims. Preferably, the part of the human or animal body is a tooth.

Various aspects of the present invention will now be described by way of example only, and with reference to the accompanying drawing, FIG. 1, which shows a non-ionizing, non-scanning imager.

FIG. 1 shows a non-ionizing, non-scanning imager 10 that is capable of projecting an array of collimated infrared beamlets onto a detector. This allows imaging of, and or through, soft tissue, bone and tooth tissue. The imager 10 of FIG. 1 has a non-ionizing light source that is positioned at the focal point of a collimating lens. The source may be an LED, laser diode or thermal source or any other suitable non-ionizing radiation source.

On the optical path from the lens is a digital mirror that has a plurality of individual reflecting elements or pixels. The digital mirror may be of any suitable form, for example, a Texas Instruments Digital Mirror having 1076×756 individual mirrors each around 10 microns by 7 microns. Each mirror is individually switchable between an on and off position at up to 100 kHz. Light that passes through the lens is collimated and directed onto the digital mirror. With all the mirrors in the on position the complete collimated beam would be reflected to form a plurality of collimated beamlets. Alternatively, individual beamlets or selected groups of beamlets can be reflected.

On the reflection path from the digital mirror is a detector, for example a CCD camera, which has a plurality of detector elements or pixels. The emitter and detector are arranged such that there is correlation between the emitting and detecting pixels. This correlation is effected by coding the light using, for example, a computer. At some point, typically at start-up with no sample between the mirror and camera, the beamlets are switched on in turn and mapped to one or more detector pixels. The beamlets are arranged and sized so that no detector pixel receives unscattered radiation from more than one beamlet, although a single beamlet may extend over more than one detector pixel. The correlation information is then stored and used when the beamlets are activated again. The correlation can be temporal as well as spatial, i.e. an image can be formed from one or more pixels.

Once the system is set up and a sample is being imaged, ballistic photons go straight through the sample to the mapped pixel or pixels, and scattered light is diverted into others. Because each detector pixel is set up to receive unscattered radiation from only a single beamlet, scattered radiation can be identified. The level and position of the scattered photons are recorded as this helps to determine the scattering properties of the sample. This information can be used to provide an indication of the sample structure.

Connected to both the digital mirror and the detector is a computer processor, typically a PC, which has software for analyzing the light that is reflected from each element/pixel of the digital mirror and detected signals, thereby to form an image. Because ballistic and scattered photons can be distinguished, the contrast, and hence quality of the infrared transmission images is increased.

In use, a sample is placed in the space between the mirror array and the camera. Alternatively for oral and dental applications either the light source or the detector may be placed inside the oral cavity around the point of interest. Then, the pixels are switched on either in groups or individually. To avoid cross talk, typically adjacent groups are not switched on simultaneously. The light falling on each corresponding camera pixel is then recorded and the next pixel array switched on and its corresponding signal recorded. Thus, only directly transmitted light is detected. After each pair of pixels has been switched on and the signal recorded the image can be displayed. Using collimated beamlets enhances the local effects of scattering centres in the sample, thereby providing images with greater contrast and apparent resolution.

Whilst in the system described above, light is provided from a single high power LED, it could equally be from a laser, such as a laser diode, or from a conventional thermal light source (bulb). The source could be an array of such sources such as an LED micro-array or VCSEL array, provided each beam or group of beams can be mapped onto the detector. In principle, a scanning disc containing an array of holes could be used if it was known exactly which hole was present in front of the source at any one time and hence which detector pixel should be used. Light at around 810 nm is preferred for some oral and dental applications. Where high-resolution images of teeth are required, light in the range of 1100 nm to 1300 nm is preferred. However, other wavelengths could be used to potentially detect other items and to pass through other tissue types.

The imaging method of the present invention offers a significant increase in the contrast of IR images. By investigating the interpretation of the scattered as well as unscattered photons, additional information about the scattering object is provided. For example, scattering will change as a lesion dries out and this rate of change will provide some information on the state of a carious lesion. Thus, the invention provides significantly higher sensitivity to early lesions/tissue changes.

The invention makes it possible to image in vivo through the jaws (skin, muscle, gums and bone) to image the developing dentition, which is important in orthodontic and developmental assessments. In particular, the invention makes it possible to image hard dental tissue, in vivo with high image quality. More specifically, the dental tissue that can be imaged includes: 1) carious lesions, including at the early stages 2) the enamel dentine junction, hence image enamel thickness and 3) the root canal system through the gum and bone, offering the possibility of continual assessment during root canal therapy. Other body parts can also be imaged, such as other parts of the head and neck, as well as limbs and possibly parts of the torso. This can all be done without the need for x-rays, thereby offering significant advantages over conventional radiography in terms of health hazards.

A skilled person will appreciate that variations of the disclosed arrangements are possible without departing from the invention. For example, the light source and or detector may be located some distance from the object to be imaged. In this case, suitable means can be used to transmit the beamlets to and/or from the points on either side of the object. For example, the system could be used endoscopically with arrayed fibres delivering and/or receiving the light from a remote source/detector. In addition, although the invention has been described with reference to two-dimensional imaging, separate images taken at different angles could be captured and processed to generate 3-D images. Accordingly the above description of the specific embodiment is made by way of example only and not for the purposes of limitation. It will be clear to the skilled person that minor modifications may be made without significant changes to the operation described.

The invention claimed is:

1. A medical imager comprising:
   a source comprising at least one of a fiber array, a pixelated device, a digital mirror that has a plurality of mirror pixels, a plurality of light emitting elements, or at least one LED positioned at the focal point of a collimating lens, configured for providing a plurality of collimated beams of non-ionizing radiation to at least one of a sample of a biological material or a part of a human or animal body;
   a plurality of detectors, wherein each of said plurality of collimated beams is mapped to at least one detector so that each detector is configured to receive only unscattered light from only its mapped beam or scattered light from one or more other beams; and
   a computer processor configured to:
      cause the source to provide at least one of one collimated beam or a group of collimated beams selected to avoid cross talk for passing through a sample for detection by the plurality of detectors;
      identify light detected at one or more detectors mapped to the collimated beam or beams as the unscattered light, and identify light at other detectors as the scattered light; and
      use both the unscattered and scattered light to form an image.

2. An imager as claimed in claim 1, wherein the source is a laser, LED or thermal source.

3. An imager as claimed in claim 1, wherein the source is pixelated or is directed onto a device that produces an array of beamlets.

4. An imager as claimed in claim 1, wherein said computer processor is further configured for switching on simultaneously all or selected groups of the individual beams.

5. An imager as claimed in claim 1, wherein the non-ionizing radiation is an infrared radiation.

6. An imager as claimed in claim 5, wherein the non-ionizing radiation is in the range 810 nm to 850 nm.

7. An imager as claimed in claim 5, wherein the non-ionizing radiation is in the range 1100 nm to 1300 nm.

8. An imager as claimed in claim 5, wherein the non-ionizing radiation is in the near infra-red.

9. An imager as claimed in claim 1, wherein at least one of the unscattered light or the scattered light is temporally incoherent.

10. An imager as claimed in claim 1, wherein at least one of the unscattered light or the scattered light is temporally coherent.

11. An imager as claimed in claim 1, further comprising one or more filters for preferentially selecting an incident non-ionizing radiation.

12. An imager as claimed in claim 1, wherein the imager is configured for oral and/or dental applications.

13. A method for imaging biological material, said method comprising the steps of:
    illuminating a sample of a biological material using a plurality of collimated beams of non-ionizing radiation;
    detecting the non-ionizing radiation that has passed through the sample using a plurality of detectors, wherein each of said plurality of collimated beams is mapped to at least one detector so that each detector is configured to receive only unscattered light from only its mapped beam or scattered light from one or more other beams;
    selecting, via a computer processor, at least one of one collimated beam or a group of collimated beams configured to avoid cross talk and for passing through a sample for detection by the plurality of detectors;
    identifying, via the computer processor, light detected at one or more detectors mapped to the collimated beam or beams as the unscattered light, and light at other detectors as the scattered light; and
    using, via the computer processor, both the unscattered and scattered light to form an image.

14. A method as claimed in claim 13, wherein the sample is illuminated in vivo.

15. A method as claimed in claim 14, wherein the sample is an oral or dental sample.

16. A method as claimed in claim 13, further comprising selecting one or more wavelengths for identifying and quantifying the presence of blood and/or small blood vessels in particular regions of an image.

17. A method as claimed in claim 16, wherein the selected one or more wavelengths are in the wavelength range of 810 nm to 850 nm.

18. A method as claimed in claim 16, further comprising using the identification of blood and/or small blood vessels to identify regions of inflammation.

19. A method of diagnosis of a part of a human or animal body, said method comprising the steps of:
    illuminating the part using a plurality of collimated beams of non-ionizing radiation,
    detecting the non-ionizing radiation that has passed through the part using a plurality of detectors, wherein each of said plurality of collimated beams is mapped to at least one detector so that each detector is configured to receive only unscattered light from only its mapped beam or beams and scattered light from one or more other beams,
    selecting, via a computer processor, at least one of one collimated beam or a group of collimated beams configured to avoid cross talk and for passing through the part for detection by the plurality of detectors;
    identifying, via the computer processor, light detected at one or more detectors mapped to the collimated beam or beams as the unscattered light, and light at other detectors as the scattered light;
    using, via the computer processor, both the unscattered and scattered light to form an image, and
    providing a diagnosis of the part of the human or animal body using said image.

20. A method as claimed in claim 19, wherein the part of the human or animal body is a tooth.

* * * * *